(12) United States Patent (10) Patent No.: US 9,394,563 B2
Quarder et al. (45) Date of Patent: Jul. 19, 2016

(54) ELECTRODE SYSTEM FOR MEASURING AN ANALYTE CONCENTRATION UNDER IN-VIVO CONDITIONS

(75) Inventors: Ortrud Quarder, Heidelberg (DE);
Arnulf Staib, Heppenheim (DE);
Reinhold Mischler, Ludwigshafen (DE);
Ewald Rieger, Bobenheim-Roxheim (DE); Ralph Gillen, Papenburg (DE);
Ulrike Kamecke, Mannheim (DE)

(73) Assignee: Roche Diabetes Care, Inc., Indianapolis, IN (US)

(*) Notice: Subject to any disclaimer, the term of this patent is extended or adjusted under 35 U.S.C. 154(b) by 780 days.

(21) Appl. No.: 13/042,773

(22) Filed: Mar. 8, 2011

(65) Prior Publication Data

US 2011/0196216 A1 Aug. 11, 2011

Related U.S. Application Data

(63) Continuation of application No. PCT/EP2009/003758, filed on May 27, 2009.

(30) Foreign Application Priority Data

Sep. 11, 2008 (EP) .................................... 08015982

(51) Int. Cl.
*A61B 5/05* (2006.01)
*A61B 5/04* (2006.01)
(Continued)

(52) U.S. Cl.
CPC ............ *C12Q 1/001* (2013.01); *A61B 5/14532* (2013.01); *A61B 5/14865* (2013.01); *A61B 5/7207* (2013.01)

(58) Field of Classification Search
USPC .................................................. 600/345–372
See application file for complete search history.

(56) References Cited

U.S. PATENT DOCUMENTS 4,076,596 A * 2/1978 Connery et al. .............. 205/780
4,655,880 A * 4/1987 Liu ............................. 205/777.5
(Continued)

FOREIGN PATENT DOCUMENTS

EP 1 733 676 A1 6/2005
EP 1 785 085 A1 11/2005
(Continued)

OTHER PUBLICATIONS

Maya Zayats et al., Reconstitution of Apo-Glucose Dehydrogenase on Pyrroloquinoline Quinone-Functionalized Au Nanoparticles Yields an Electrically Contacted Biocatalyst, J. Am. Chem. Soc., Published on Web Aug. 13, 2005, pp. 12400-12406, vol. 127 No. 35, Copyright 2005 American Chemical Society.
(Continued)

*Primary Examiner* — Michael Kahelin
*Assistant Examiner* — Mitchell E Alter

(57) ABSTRACT

An electrode system for measuring the concentration of an analyte under in-vivo conditions comprises a counter-electrode having an electrical conductor, a working electrode having an electrical conductor on which an enzyme layer containing immobilized enzyme molecules for catalytic conversion of the analyte is arranged, and a diffusion barrier that slows the diffusion of the analyte from body fluid surrounding the electrode system to enzyme molecules. The enzyme layer is in the form of multiple fields that are arranged on the conductor of the working electrode at a distance from each other.

27 Claims, 4 Drawing Sheets

(51) Int. Cl.
  *C12Q 1/00* (2006.01)
  *A61B 5/145* (2006.01)
  *A61B 5/1486* (2006.01)
  *A61B 5/00* (2006.01)

(56) References Cited

U.S. PATENT DOCUMENTS

| | | | |
|---|---|---|---|
| 5,089,112 A * | 2/1992 | Skotheim | C12Q 1/004 204/403.1 |
| 6,083,366 A | 7/2000 | Higson | |
| 6,175,752 B1 | 1/2001 | Say et al. | |
| 6,212,416 B1 | 4/2001 | Ward et al. | |
| 6,284,126 B1 * | 9/2001 | Kurnik et al. | 205/777.5 |
| 2002/0120186 A1 | 8/2002 | Keimel | |
| 2002/0156355 A1 * | 10/2002 | Gough | A61B 5/14532 600/345 |
| 2004/0043527 A1 | 3/2004 | Bradley et al. | |
| 2005/0059871 A1 | 3/2005 | Gough et al. | |
| 2005/0272989 A1 | 12/2005 | Shah et al. | |
| 2006/0004272 A1 | 1/2006 | Shah et al. | |
| 2007/0151868 A1 | 7/2007 | Staib et al. | |
| 2007/0170073 A1 * | 7/2007 | Wang et al. | 205/775 |
| 2007/0208243 A1 * | 9/2007 | Gabriel | A61B 5/14532 600/347 |
| 2007/0227907 A1 * | 10/2007 | Shah | G01N 27/307 205/777.5 |
| 2008/0156646 A1 | 7/2008 | Wu et al. | |
| 2010/0113976 A1 | 5/2010 | Wahl et al. | |

FOREIGN PATENT DOCUMENTS

| | | |
|---|---|---|
| WO | WO 99/45375 | 9/1999 |
| WO | WO 2005/010518 | 2/2005 |
| WO | WO 2005/086724 | 9/2005 |
| WO | WO 2005/121759 | 12/2005 |
| WO | WO 2007/026152 | 3/2007 |
| WO | WO 2007/147475 | 12/2007 |
| WO | WO 2008/104397 A2 | 9/2008 |
| WO | WO 2010/028708 | 3/2010 |

OTHER PUBLICATIONS

Katja Habermuller et al., Conducting Redoxpolymer-Based Reagentless Biosensors Using Modified PQQ-Dependent Glucose Dehydrogenase, Microchim. Acta 143, Received May 18, 2003; Accepted Jun. 12, 2003; Published online Nov. 17, 2003, pp. 113-121, Copyright Springer-Verlag 2003.

Noriko Kakehi et al., A novel wireless glucose sensor employing direct electron transfer principle based enzyme fuel cell. Bioserisors and Bioelectronics 22, Received Apr. 24, 2006; Received in revised form Sep. 20, 2006; Accepted Nov. 9, 2006; Available online Dec. 12, 2006, pp. 2250-2255, Copyright 2006 Elsevier B.V.

Arthur Oubrie, Structure and mechanism of soluble glucose dehydrogenase and other PQQ-dependent enzymes, Biochimica et Biophysica Acta 1647, Received Jun. 17, 2002; Accepted Jan. 22, 2003, pp. 143-151, Copyright 2003 Elsevier Science B.V.

Asavapiriyanont, S. et al., "The Electrodeposition of Poly-N-Methylpyrrole Films from Aqueous Solutions," Journal of Electroanalytical Chemistry, 1984, pp. 245-251, vol. 177.

Fears, Kenan P. et al., "Residue-Dependent Adsorption of Model Oligopeptides on Gold," Journal of the American Chemical Society, 2013, pp. 15040-15052, vol. 135.

Indole Material Safety Data Sheet, #63387, Acros Organics, 2009, 4 pages.

Luminol Safety Data Sheet, Carolina, 2013, 4 pages.

Marchesi, L. F. Q. P. et al., "Investigation of Polypyrrole Degradation Using Electrochemical Impedance Spectroscopy," The Journal of Physical Chemistry B, 2011, pp. 9570-9575, vol. 115.

Neoh, K. G. et al., "Structural and Mechanical Degradation of Polypyrrole Films Due to Aqueous Media and Heat Treatment and the Subsequent Redoping Characteristics," John Wiley & Sons, Inc., 1997, pp. 519-526.

Sadki, Said et al., "The mechanisms of pyrrole electropolymerization," Chemical Society Review, 2000, pp. 283-293, vol. 29.

Saraji, M. and Bagheri, A., "Electropolymerization of indole and study of electrochemical behavior of the polymer in aqueous solutions," Synthetic Metals, 1998, pp. 57-63, vol. 98.

Cui, C. Q. et al., "Extent of Incorporation of Hydrolysis Products in Polyaniline Films Deposited by Cyclic Potential Sweep," Electrochimica Acta, 1993, pp. 1395-1404, vol. 38, No. 10.

Patnaik, Pradyot, A Comprehensive Guide to the Hazardous Properties of Chemical Substances, 2007, pp. 252-253, 486-491, John Wiley & Sons, Inc., New Jersey.

* cited by examiner

400
ELECTRODE SYSTEM FOR MEASURING AN ANALYTE CONCENTRATION UNDER IN-VIVO CONDITIONS

CROSS-REFERENCE TO RELATED APPLICATIONS

This application is a continuation of International Application No. PCT/EP2009/003758 filed May 27, 2009, which claims priority to EP Application No. 08015982.5 filed Sep. 11, 2008. Each of the referenced applications is incorporated herein by reference in its entirety.

TECHNICAL FIELD

The invention relates to an electrode system for measuring an analyte concentration under in-vivo conditions.

BACKGROUND

Sensors with implantable or insertable electrode systems facilitate measurements to be made of physiologically significant analytes such as, for example, lactate or glucose in a patient's body tissue. The working electrodes of systems of this type have electrically conductive enzyme layers in which enzyme molecules are bound which release charge carriers by catalytic conversion of analyte molecules. In the process, an electrical current is generated as measuring signal whose amplitude correlates to the analyte concentration.

The electrical conductivity of good enzyme layers should be as high as possible to allow charge carriers that are released to be detected as measuring signal as completely as possible, they should be sufficiently water-permeable to allow analyte molecules to diffuse from aqueous body fluid, usually this will be interstitial fluid or blood, into the enzyme layer, and finally they should bind enzyme molecules contained therein as completely as possible such that these cannot leak into surrounding body tissue.

Suitable enzyme layers can be made, for example, of platinum black, which can be impregnated with enzyme solution and shows good water permeability because of its sponge-like structure, or from electrically conductive particles, for example carbon or metal particles, and a binding agent. Enzyme layers of this type are usually brittle. For this reason, the enzyme layer of the working electrode of known sensors covers only a very small area, usually only a fraction of a square millimeter. An example of this is the electrode system known from U.S. Pat. No. 4,655,880, in which the conductor of the working electrode extends over only approximately 200 µm. In order to increase the local current density, this conductor is provided with an electrically insulating coating into which small openings with a diameter of approximately 10 µm were etched before the conductor was coated over its entire length with an enzyme-containing paste in order to form an enzyme layer.

However, despite extensive research and development, known electrode systems are susceptible to interference and associated with a disadvantage in that they can be used to determine the analyte concentration only at lower accuracy and reliability than is feasible using a conventional ex-vivo analysis.

In order to increase the measuring accuracy, US 2005/0059871 A1 proposes to measure the analyte concentration of interest using multiple working electrodes simultaneously and to statistically analyze the measurements thus obtained. As an additional measure, it is proposed to use further sensors to determine other analyte concentrations or physiological parameters and test the plausibility of individual results based on the concentration of different analytes thus obtained.

However, the use of a large number of working electrodes not only increases the utilization of equipment resources, but also leads to a problem if inconsistent measuring signals of the individual working electrodes make it unclear which of the different measuring values accurately reflect the analyte concentration in the body of the patient.

SUMMARY

The invention provides ways of measuring analyte concentrations in a human or animal body more reliably and more accurately. The invention includes an electrode system for in-vivo measurement of the concentration of an analyte. The electrode system includes a counter-electrode having an electrical conductor and a working electrode having an electrical conductor on which an enzyme layer containing immobilized enzyme molecules for catalytic conversion of the analyte is arranged. The working electrode also includes a diffusion barrier that slows the diffusion of the analyte from body fluid surrounding the electrode system to the enzyme molecules.

According to one aspect of the invention, the enzyme layer of the working electrode is in the form of multiple fields that are arranged at a distance from each other on the conductor of the working electrode. In one refinement of this aspect, at least two of these fields are spaced at least 3 millimeters, alternatively at least 5 millimeters, distant from each other. For example, a series of multiple fields can be provided, whereby the distance between the first and the last field of the series is larger than 5 millimeters. The individual fields of a working electrode can basically form a series of working electrodes that are arranged in series. Between these fields, the conductor of the working electrode may be covered by an insulation layer. By arranging the fields of the enzyme layer on top of openings of an electrically insulating layer the signal-to-noise ratio can be improved.

The invention allows significantly more reliable measurements of an analyte concentration in a patient's body tissue to be made. By providing the enzyme layer of a working electrode in the form of individual fields, for example, over a distance of at least 3 millimeters, or alternatively at least 5 millimeters, the analyte concentration can to be measured in a correspondingly large volume. Interfering influences that affect only a small volume element with a diameter of approximately 0.1 mm are therefore insignificant with an electrode system according to the invention. Surprisingly, a major fraction of the problems observed during in-vivo measurements using known sensors appear to be based simply on the fact that, due to the small size of the enzyme layer, the analyte concentration was measured in a volume element that was so small that it was often not representative for the rest of the patient's body due to transient local effects.

For expansion of the enzyme layer over a long distance of a few millimeters and more, the working electrode can be flexible such that it can adjust its shape to movements of the body. However, the relatively brittle properties of the material of known conductive enzyme layers appear to render a flexible working electrode impossible to make. However, the measure according to the invention, namely to design the enzyme layer in the form of multiple fields that are arranged at a distance from each other on the conductor of the working electrode, allows the working electrode to be bendable without the enzyme layer flaking off despite the brittle properties of the enzyme layer material.

The cause for measurements with conventional working electrodes whose effective area, i.e. the enzyme layer, extends over less than 0.2 square millimeters, to be erroneous is presumed to be that movements of a patient can transiently prevent fluid exchange in a small volume element, for example by cells being pressed against the working electrode and interstitial fluid being displaced or by capillary vessels being compressed and thereby obstructed. Presumably, this may lead to the analyte concentration in the corresponding volume element in the immediate surrounding of the working electrode not being representative of the rest of the patient's body. These volume elements, in which a fluid exchange is transiently prevented, appear to be very small, though, and usually have a diameter of less than 1 mm. It is likely that the elastic and soft consistency of body tissue allows forces to relax over very short distances and the exchange of body fluid is therefore adversely affected only in volume elements that are this small in size. Having at least some of the fields forming the enzyme layer in an electrode system according to the invention being distributed over a substantial distance, for example at least 5 mm distant from each other, or alternatively at least 1 cm distant from each other, therefore provides for only a small, and usually negligible, part of the working electrode being adversely affected even in the most unfavorable case.

In this context, the distance between two fields of the enzyme layer of a working electrode is to be measured from the edge of the one field to the other field's edge facing it.

In this context, the distance between adjacent fields is at least 0.3 millimeters, in particular at least 0.5 millimeters. The individual fields each extend less than two millimeters, or less than one millimeter, in particular less than 0.6 millimeter, in two directions that are perpendicular to each other. The fields can, for example, be circles with a diameter of less than 1 millimeter or rectangles with an edge length of less than 1 millimeter. The fields can be arranged in a row on the conductor of the working electrode. However, it is also feasible, for example, to arrange the fields in several rows and columns on a circular or rectangular conductor. The number of fields can be selected virtually freely. However, the working electrode in one form has at least 5 fields.

The working electrode of the electrode system is provided with a diffusion barrier that decelerates the diffusion of the analyte from the body fluid surrounding the electrode system to enzyme molecules that are immobilized in the enzyme layer. The diffusion barrier can, for example, be a cover layer covering the enzyme layer. However, it is feasible just as well that diffusion-inhibiting particles are incorporated into the enzyme layer to serve as diffusion barrier. For example, pores of the enzyme layer can be filled with a polymer through which analyte molecules can diffuse only slowly. Such a polymer should be hydrophilic and have a fast water uptake. A diffusion barrier can be used to reduce the consumption of analyte molecules at the working electrode. If movements of the patient transiently interfere with the exchange of body fluid in a surrounding of an enzyme layer field of the working electrode, having a lower conversion rate of analyte molecules contributes to reducing the impact of such interference. The lower the consumption of analyte, the longer it takes for depletion effects to occur, i.e. for the analyte concentration in the corresponding area to drop as a consequence of the measurements that are performed.

According to another refinement of this aspect, the working electrode includes a spacer that is arranged over the enzyme layer, as seen from the conductor, and provides for a minimal distance between the enzyme layer and body tissue that surrounds cells. The spacer forms a reservoir for analyte molecules. By this means, the impacts of a transient disturbance of the fluid exchange in the surroundings of the working electrode can be reduced further. The spacer can, for example, be a layer made of a biocompatible polymer that facilitates permeation of the analyte. A spacer can be used to create an analyte buffer volume from which the enzyme fields of the working electrode are supplied. In this way it can be achieved advantageously that no noticeable adverse effect on the measuring signal occurs even in the presence of substantial disturbance of the fluid exchange in the surrounding of an enzyme layer field for a period of half an hour. The spacer can just as well be provided, for example, as a porous membrane, for example a dialysis membrane, or a mesh. The spacer preferably is 3 micrometers to 30 micrometers thick. The spacer can be arranged on a diffusion-inhibiting cover layer. However, it is feasible just as well to arrange the spacer directly on the enzyme layer. In this context, the spacer can also act as diffusion barrier and slow down the diffusion of analyte molecules to the enzyme layer.

The spacer can cover the working electrode and the counter-electrode and, if one is present, the reference electrode in the form of a continuous layer. The spacer can cover the entire implanted surface of the substrate. If the spacer is made of a biocompatible material, the tissue response to the implant can be reduced. Independent of this, it is also contemplated for the spacer to be arranged on a diffusion-inhibiting cover layer and to be more hydrophilic than the cover layer.

Like the electrical conductor of the counter-electrode of the electrode system, the electrical conductor of the working electrode can be designed as a conductor path on a substrate, for example a conductor path made of metal or graphite on a plastic plate. However, it is feasible just as well to design the conductor in the form of wires. The enzyme layer fields can be arranged on a conductor that is designed in the form of a wire, for example, in the form of ring-shaped segments. In the case of ring-shaped segments on a wire, the object explained above, namely that the individual fields each extend less than 2 millimeters, or alternatively less than one millimeter, in particular less than 0.6 millimeter, in two directions that are perpendicular to each other, must be understood to mean that the width of the ring and its diameter are the two directions that are perpendicular to each other.

The use of metallic wires and conductor paths on a substrate allows a flexible sensor to be designed that can be bent by 90 degrees and more inside the body of a patient without breaking.

It is common for conductor paths to extend on a single side of the substrate only. However, in principle it is feasible just as well for a single conductor to extend on opposite sides of the substrate, for example through a bore hole or around a lateral edge.

Another refinement of this aspect of the invention provides the enzyme to interact in the enzyme layer with a catalytic redox mediator that reduces or prevents an oxygen dependence of the catalytic conversion of the analyte. Catalytic redox mediators of this type are sometimes also called electro-catalysts since they favor the transfer of electrons to conductive components of the working electrode, for example graphite particles in the enzyme layer. For example manganese dioxide, in the form of pyrolusite, or other metal oxides which oxidize hydrogen peroxide catalytically and, in the process, transfer electrons to conductive components of the working electrode can be used as catalytic redox mediators. A catalytic redox mediator in the form of a metal oxide can lower the potential of the working electrode by more than 100 millivolts such that the influence of interfering substances, for example ascorbate or uric acid, on the measuring signal is reduced significantly. In the case of enzymes that oxidize analyte molecules and generate hydrogen peroxide in the process, the use of a catalytic redox mediator of this type allows to counteract the depletion of oxygen in the surroundings of the working electrode and therefore provides for the conversion rate to depend only on the analyte concentration, but not on the oxygen concentration, over a wide range of concentrations.

Organometallic compounds, for example cobalt-phthalocyanine, are also suitable as catalytic redox mediators that degrade hydrogen peroxide. The catalytic redox mediator can be bound covalently to the enzyme molecule or be embedded in the enzyme layer, for example in the form of separate particles.

However, it is also feasible for the catalytic redox mediator to effect a direct electron transfer. By this means, having a catalytic redox mediator that is covalently bound to the enzyme can be used to effect an oxidation of analyte molecules and an electron transfer to the working electrode without the intermediate step of generating hydrogen peroxide. In a direct electron transfer, an electron from a prosthetic group of the enzyme is transferred directly to the catalytic redox mediator and from there to a conductive component of the working electrode, for example graphite or metal particles in the enzyme layer.

A direct electron transfer can be effected, for example, with enzymes such as dehydrogenases that have pyrroloquinolinequinone (PQQ) as the prosthetic group. In the case of glucose dehydrogenase (GlucDH) from Acinetobacter calcoaceticus, PQQ is transferred to a reduced state by the enzyme during the oxidation of glucose. This prosthetic group can be covalently bound directly to a conductor by means of gold nanoparticles in order to facilitate a direct electron transfer from reduced PQQ to the conductor. Apparently, oxygen does not react with reduced PQQ, which means that it does not compete with the electron transfer. Another way of transferring the electrons from reduced PQQ is based on the insight that PQQ itself can be present in multiple oxidation stages

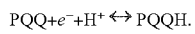

PQQ+$e^-$+$H^+$ ↔ PQQH.

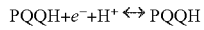

PQQH+$e^-$+$H^+$ ↔ PQQH and can therefore be used as catalytic redox mediator. Accordingly, additional PQQ molecules can be bound covalently on the GlucDH enzyme and serve to receive electrons from a catalytically active pocket of the protein, i.e. from the prosthetic group of PQQ present therein. Another option is based on a variant of GlucDH (from Burkholderia cepacia), which has flavine-adenine-dinucleotide (FAD) as prosthetic group, and has the cytochrome C protein in another sub-unit, that can transfer electrons from $FADH_2$.

The electrode system can have, in addition, a reference electrode. The reference electrode can supply a reference potential for the working electrode that is defined, for example, by the silver/silver chloride redox system. Moreover, the electrode system can further have electrodes, for example additional working electrodes, in particular working electrodes with different measuring sensitivity as is described in US 2007/0151868 A1, which is incorporated herein by reference.

Combined with a potentiostat that is connected to the electrode system and an amplifier for amplification of measuring signals, an electrode system according to the invention forms a sensor. The amplifier and the potentiostat can be arranged on a printed circuit board that carries the conductors of the counter-electrode and working electrode. The electrodes can be arranged on a substrate, for example, in the form of a plastic plate whose one end is attached to the circuit board. It is feasible just as well to integrate a printed circuit board into the substrate on which the electrodes are arranged. The potentiostat and the pre-amplifier can, for example, be arranged on a flexible plastic plate which simultaneously forms a printed circuit board and a substrate for conductor paths of the electrode system.

Another aspect of the invention refers to an electrode system for measuring the concentration of an analyte under in-vivo conditions, comprising a counter-electrode having an electrical conductor, a working electrode having an electrical conductor on which an enzyme layer containing immobilized enzyme molecules for catalytic conversion of the analyte is arranged, and a diffusion barrier that slows the diffusion of the analyte from body fluid surrounding the electrode system to the enzyme molecules, wherein the diffusion barrier is a layer covering the enzyme layer, and the diffusion barrier is made of a mixture of at least two polymers. The enzyme layer of such an electrode system is preferably—but not necessarily—designed in the form of multiple fields.

The diffusion barrier of such an electrode system is a solid solution of at least two different polymers, such as a solid solution of acrylates. Therefore, the diffusion barrier can combine favorable properties of different polymers with respect to permeability, water uptake, swelling and flexibility. One or all of the polymers may be an acrylate. Preferably one or all of the polymers is a copolymer, especially a copolymer of hydroxyethylmethacrylate. A copolymer is a polymer made by polymerization of at least two different monomers. It has been found that hydroxyethylmethacrylate has a very favorable water uptake combined with minor swelling.

A mixture of polymers which have a different glass transition temperature can be used for the diffusion barrier. For example one polymer may have a glass transition temperature less than 90° C., especially less than 70° C., whereas the other polymer has a glass transition temperature of more than 100° C., especially more than 110° C. The glass transition temperature is measured by differential scanning calorimetry using a heating rate of 10 K per minute.

For example the diffusion barrier may be a mixture of a copolymer of methylmethacrylate and hydroxyethylmethacrylate with a copolymer of butylmethacrylate and hydroxyethylmethacrylate. Such a mixture may for example comprise 5 to 50% percent by weight of a copolymer of butylmethacrylate and hydroxyethylmethacrylate to achieve good flexibility of the diffusion barrier.

BRIEF DESCRIPTION OF THE DRAWINGS

Further details of the invention are explained based on an exemplary embodiment making reference to the appended drawings. In the figures.

DETAILED DESCRIPTION

Figure 1:
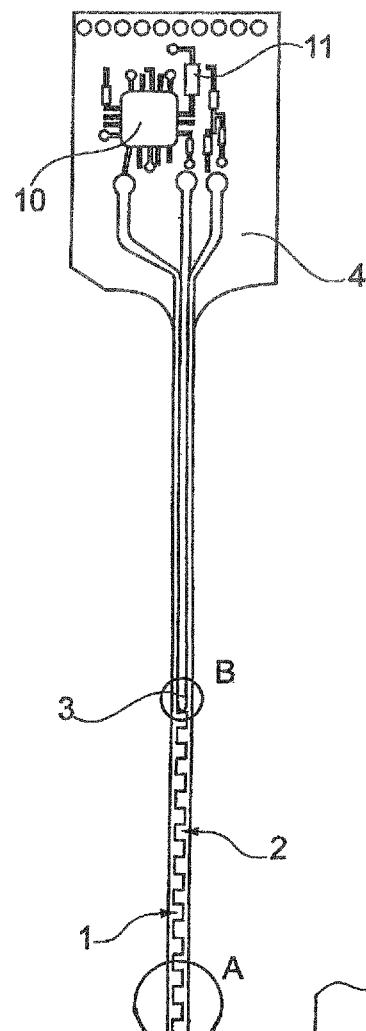
FIG. 1: shows an exemplary embodiment of an electrode system according to the invention.
Figure 2:
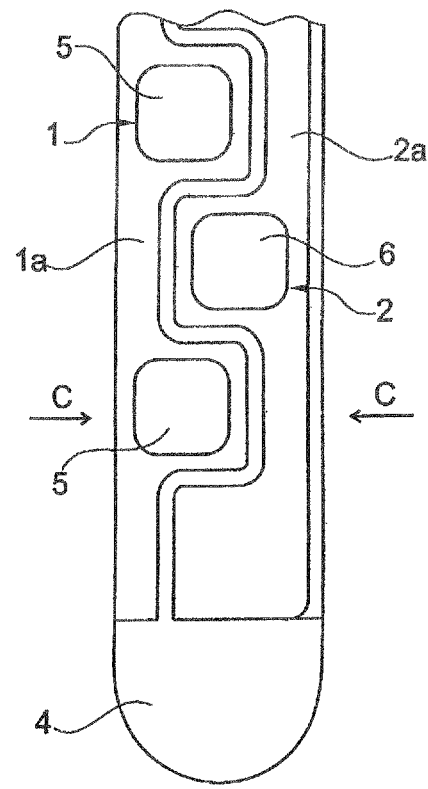
FIG. 2: shows a detail view of FIG. 1.
Figure 3:
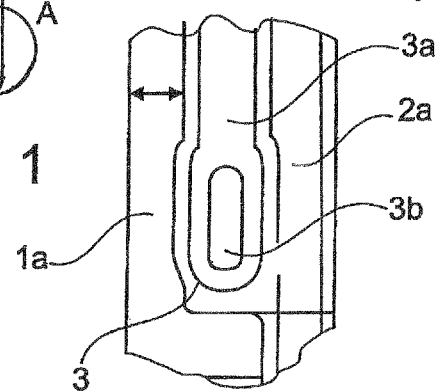
FIG. 3: shows another detail view of FIG. 1.
Figure 4:
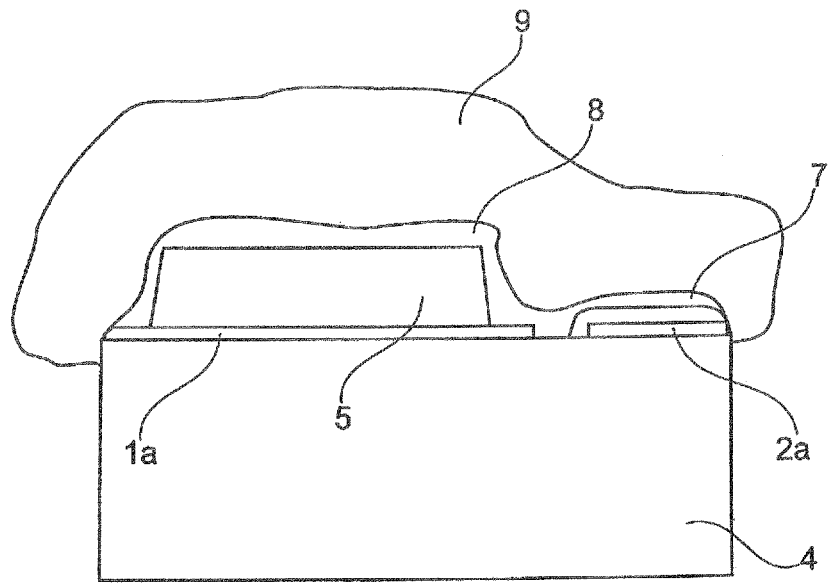
FIG. 4: shows a section along the section line, CC, of FIG. 2.

FIG. 1 shows an exemplary embodiment of an electrode system for insertion into body tissue of a human or animal, for example into cutis or subcutaneous fatty tissue. A magnification of detail view A is shown in FIG. 2, a magnification of detail view B is shown in FIG. 3. FIG. 4 shows a corresponding sectional view along the section line, CC, of FIG. 2.

The electrode system shown has a working electrode 1, a counter-electrode 2, and a reference electrode 3. Electrical conductors of the electrodes 1a, 2a, 3a are arranged in the form of metallic conductor paths, preferably made of palladium or gold, on a substrate 4. In the exemplary embodiment shown, the substrate 4 is a flexible plastic plate, for example made of polyester. The substrate 4 is less than 0.5 mm thick, for example 100 to 300 micrometers, and is therefore easy to bend such that it can adapt to movements of surrounding body tissue after its insertion. The substrate 4 has a narrow shaft for insertion into body tissue of a patient and a wide head for connection to an electronic system that is arranged outside the body. The shaft of the substrate 4 in one embodiment is at least 1 cm in length. In another embodiment, shaft of substrate 4 ranges in length from 2 cm to 5 cm.

In the exemplary embodiment shown, one part of the measuring facility, namely the head of the substrate, projects from the body of a patient during use. Alternatively, it is feasible just as well, though, to implant the entire measuring facility and transmit measuring data in a wireless fashion to a receiver that is arranged outside the body.

The working electrode 1 carries an enzyme layer 5 that contains immobilized enzyme molecules for catalytic conversion of the analyte. The enzyme layer 5 can be applied, for example, in the form of a curing paste of carbon particles, a polymeric binding agent, and enzyme molecules. Details of the production of an enzyme layer 5 of this type are disclosed, for example, in WO 2007/147475, reference to which is be made in this context and which is incorporated herein by reference. The analyte to be measured can, for example, be glucose, lactate or other medically significant molecules. Usually, an oxidase is used as enzyme, for example a glucose oxidase or lactate oxidase, or a dehydrogenase, for example a glucose dehydrogenase.

In the exemplary embodiment shown, the enzyme layer 5 is not applied continuously on the conductor 1a of the working electrode 1, but rather in the form of individual fields that are arranged at a distance from each other. Although the enzyme layer 5 is brittle, this means allows that the electrode system can be bent without the enzyme layer 5 flaking of. The electrode system shown can therefore be bent by more than 90° without breaking such that it can adapt to body movements after its insertion.

The individual fields of the enzyme layer 5 in the exemplary embodiment shown are arranged in a series, whereby there is a distance between the first and the last field of this series of more than 1 cm. There is a distance of at least 0.3 mm, in particular more than 0.5 mm, between neighboring fields each, whereby the distance is to be measured from the edge of one field to the edge of the other field. The individual fields each extend 0.2 mm to 0.6 mm, for example 0.2 mm to 0.4 mm in two directions that are perpendicular to each other. The shape of the fields can, for example, be circular or square. The total area of all fields taken together can be chosen virtually freely. In general, a total area of less than 1 square millimeter is sufficient. The total area in the exemplary embodiment shown is approximately 0.4 to 0.6 square millimeters.

The conductor 1a of the working electrode 1 has narrow sites between the enzyme layer fields that are seen particularly well in FIG. 2. The conductor 2a of the counter-electrode 2 has a contour that follows the course of the conductor 1a of the working electrode 1. This means results in an intercalating or interlocked arrangement of working electrode 1 and counter-electrode 2 with advantageously short current paths and low current density. The conductor 1a of the working electrode 1 of the exemplary embodiment shown is designed to be relatively narrow and has a width of less than 1 mm. In the exemplary embodiment shown, the conductor 1a has a width of less than 0.6 mm, namely approximately 0.3 mm to 0.5 mm, on its wide sites that are covered by fields of enzyme layer 5. At the interjacent narrow sites the conductors 1a and 2a have a width of less than 0.3 mm, namely 0.05 mm to 0.2 mm. However, an intercalating arrangement of the conductors is not obligatory. In principle, the conductors 1a, 2a can just as well be designed to be linear and have constant width.

In order to increase its effective surface, the counter-electrode 2 can be provided with a porous electrically-conductive layer 6 that is situated in the form of individual fields on the conductor 2a of the counter-electrode 2. Like the enzyme layer 5 of the working electrode 1, this layer 6 can be applied in the form of a curing paste of carbon particles and a polymeric binding agent. The fields of the layer 6 preferably have the same dimensions as the fields of the enzyme layer 5, although this is not obligatory. However, measures for increasing the surface of the counter-electrode can just as well be foregone and the counter-electrode 2 can just as well be designed to be a linear conductor path with no coatings of any kind.

The reference electrode 3 is arranged between the conductor 1a of the working electrode 1 and the conductor 2a of the counter-electrode 2. The reference electrode shown in FIG. 3 consists of a conductor 3a on which a field 3b of conductive silver/silver chloride paste is arranged.

FIG. 4 shows a schematic sectional view along the section line, CC, of FIG. 2. The section line. CC, extends through one of the enzyme layer fields 5 of the working electrode 1 and between the fields of the conductive layer 6 of the counter-electrode 2. Between the fields of enzyme layer 5, the conductor 1a of the working electrode 1 can be covered with an electrically insulating layer 7, like the conductor 2a of the counter-electrode 2 between the fields of the conductive layers 6, in order to prevent interfering reactions which may otherwise be catalyzed by the metal of the conductor paths 1a, 2a. The fields of the enzyme layer 5 are therefore situated in openings of the insulation layer 7. Likewise, the fields of the conductive layer 6 of the counterelectrode 2 may also be placed on top of openings of the insulation layer 7.

The enzyme layer 5 is covered by a cover layer 8 which presents a diffusion resistance to the analyte to be measured and therefore acts as a diffusion barrier. The cover layer 8 can, for example, consist of polyurethane, an acrylate, in particular a copolymer of methylmethacrylate and hydroxyethylmethacrylate, or another polymer showing minor swelling but fast water uptake. The cover layer 8 may advantageously be made of a mixture of at least two different acrylates which may each be a copolymer. Especially favorable results can be achieved by mixing a copolymer of methylmethacrylate and hydroxyethylmethacrylate with a copolymer of butylmethacrylate and hydroxyethylmethacrylate.

A favorable thickness of the cover layer 8 is, for example, 3 to 30 micrometers. Because of its diffusion resistance, the cover layer 8 causes fewer analyte molecules to reach the enzyme layer 5 per unit of time. Accordingly, the cover layer 8 reduces the rate at which analyte molecules are converted, and therefore counteracts a depletion of the analyte concentration.

The cover layer 8 extends continuously essentially over the entire area of the conductor 1a of the working electrode 1. On the cover layer 8, a biocompatible membrane is arranged as spacer 9 that establishes a minimal distance between the enzyme layer 5 and cells of surrounding body tissue. This means generates a reservoir for analyte molecules from which analyte molecules can get to the corresponding enzyme layer field 5 in case of a transient disturbance of the fluid exchange in the surroundings of an enzyme layer field 5. If the exchange of body fluid in the surroundings of the electrode system is transiently limited or even prevented, the analyte molecules stored in the spacer 9 keep diffusing to the enzyme layer 5 of the working electrode 1 where they are converted. The spacer 9 therefore causes a notable depletion of the analyte concentration and corresponding falsification of the measuring results to occur only after a significantly longer period of time. In the exemplary embodiment shown, the membrane forming the spacer 9 also covers the counter-electrode 2 and the reference electrode 3.

The spacer membrane 9 can, for example, be a dialysis membrane. In this context, a dialysis membrane is understood to be a membrane that is impermeable for molecules larger than a maximal size. The dialysis membrane can be prefabricated in a separate manufacturing process and may then be applied during the fabrication of the electrode system. The maximal size of the molecules for which the dialysis membrane is permeable is selected such that analyte molecules can pass, while larger molecules are retained.

Alternatively, instead of a dialysis membrane, a coating made of a polymer that is very permeable for the analyte and water, for example on the basis of polyurethane, can be applied over the electrode system as spacer membrane 9.

The enzyme layer 5 can contain metal oxide particles, including manganese dioxide particles, as catalytic redox mediator. Manganese dioxide catalytically converts hydrogen peroxide that is formed, for example, by enzymatic oxidation of glucose and other bioanalytes. During the degradation of hydrogen peroxide, the manganese dioxide particles transfer electrons to conductive components of the working electrode 1, for example to graphite particles in the enzyme layer 5. The catalytic degradation of hydrogen peroxide counteracts any decrease of the oxygen concentration in the enzyme layer 5. This allows the conversion of the analyte to be detected in the enzyme layer 5 to not be limited by the local oxygen concentration. The use of the catalytic redox mediator therefore counteracts a falsification of the measuring result by the oxygen concentration being low. A catalytic redox mediator also prevents the generation of cell-damaging concentrations of hydrogen peroxide.

Figure 5:
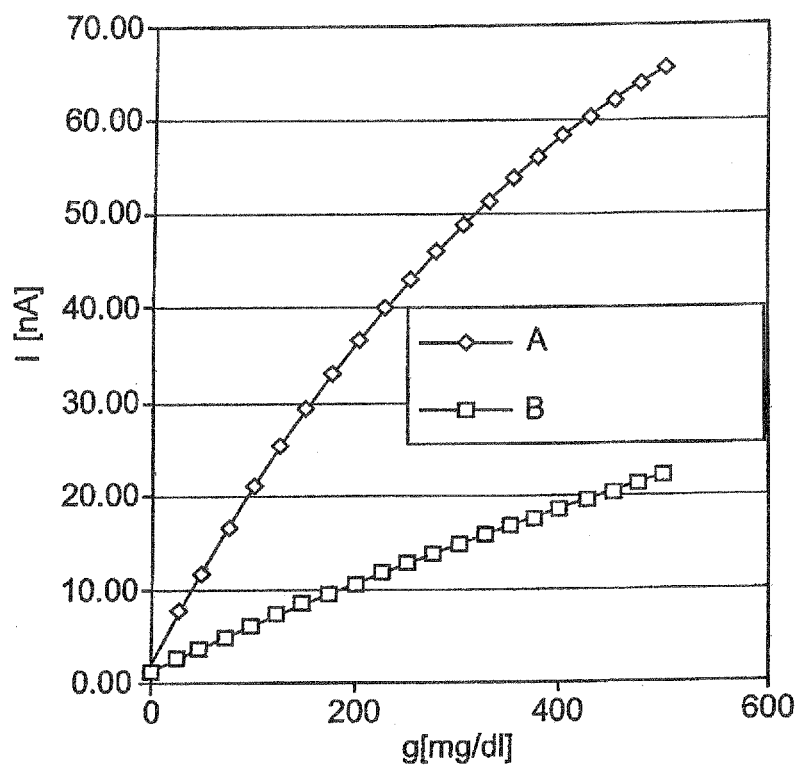
FIG. 5: shows in-vitro functional curves of the electrode system shown in FIG. 1 having a different cover layer.

FIG. 5 shows functional curves, measured under in vitro conditions, of the electrode system described above having different coating layers 8. The measured strength of the current, in nA, is plotted as a function of the glucose concentration, in mg/dl, as functional curves. The upper functional curve A was measured with an electrode system whose coating membrane 8 made of hydrophilized polyurethane has a thickness of five micrometers. For comparison, there is shown, as lower functional curve B, the dependence of the current on the glucose concentration for an electrode system having a coating membrane 8 that presents about twice the diffusion resistance to analyte molecules, for example because of a correspondingly larger thickness or lesser hydrophilization. The electrode systems of the functional curves shown in FIG. 5 were operated with a polarization voltage of 350 mV.

The hydrophilized polyurethanes (HPUs) used as coating layers can be produced by polycondensation of 4,4'-methylene-bis(cyclohexylisocyanate) and diol mixtures. The two components of the diol mixture, which were used to adjust the degree of hydrophilization of the polymer, are polyethylene glycol (PEG, MW (molecular weight)=1000 g/mol) and polypropylene glycol (PPG, MW (molecular weight)=1500 g/mol). For functional curve A, the HPU coating layer 8 was produced at a PEG to PPG ratio of 1 to 3. For the functional curve B, the HPU coating layer 8 was produced at a PEG:PPG ratio corresponding to 1:7. The cover layer 8 is approximately 5 μm thick in both cases.

For the analyte concentration in the surroundings of the electrode system to be influenced by the measurement as little as possible and to therefore be falsified no more than to a minor degree even upon a transient disturbance of the exchange of body fluid, it is advantageous to have low analyte conversion rates and therefore low measuring currents. Good results can be obtained with electrode systems that generate, with a total area of the enzyme layer of 1 $mm^2$ or less, a current of less than 50 nA, in particular less than 10 nA at a glucose concentration of 180 mg/dl. For example the electrode system of the functional curve B shown in FIG. 5 was used to measure, in the cutis of a pig, a current of 3 nA at a glucose concentration of 180 mg/dl. Measuring signals that are this small are difficult to transmit over large distances. It is therefore preferable to arrange a potentiostat and an amplifier in the immediate vicinity of the electrode system. A potentiostat 10 and an amplifier 11 can, for example, be arranged on a head of the substrate 4, as is shown in FIG. 1. It is feasible just as well to attach the substrate 4 to a conductor path board carrying the potentiostat and amplifier.

Figure 6:
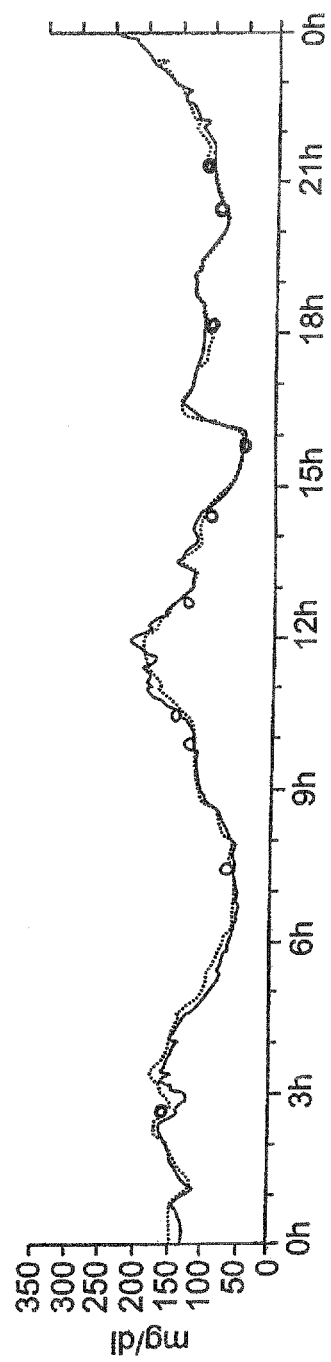
FIG. 6: shows examples of in-vivo measurements of electrode systems according to the invention.

FIG. 6 shows in-vivo measurements that were measured in the abdominal subcutaneous fatty tissue of an insulin-dependent diabetic using the two electrode systems whose functional curves are shown in FIG. 5 and which, in addition, were provided with a spacer. The two electrode systems were implanted at a distance of approximately 10 cm.

The signal characteristics of the two sensors that were implanted simultaneously shows that the results obtained using electrode systems according to the invention are highly consistent. There are no relevant deviations in the local glucose concentration between the two insertion sites. The results shown also document that there appear to exist no transient deviations in the glucose concentration between blood (circles) and tissue (solid and dotted lines).

The electric current values of the two sensors were converted to glucose values by calculation using a sampling rate of one measuring value per minute without filtering. The conversion was performed based on blood sugar values that were determined on samples of body fluid under ex-vivo conditions.

For the in-vivo measurements shown in FIG. 6, the electrode system first had a hydrophilic polyurethane cover layer 8 applied to it and was then immersed into a 12.5% ethanolic solution of the copolymer of butylmethacrylate (BMA) and 2-methacryloyloxyethyl-phosphorylcholine (MPC) (Lipidure CM5206, NOF Corp, Japan), and the coating having a thickness of 25 thus generated was then dried for 12 h. The current density is virtually unchanged by this spacer 9 made of BMA-MPC: in the absence of the spacer 9, the electrode system from FIG. 5, functional curve A, reaches approx. 40 $nA/mm^2$ at 180 mg/dl, whereas it reaches 38 $nA/mm^2$ in the presence of BMA-MPC spacer. No difference in the current amplitude can be detected at all in the case of the electrode system of functional curve B: 10 $nA/mm^2$ at 180 mg/dl in the presence as well as in the absence of spacer 9 made of BMA-MPC.

The spacer suppresses effects of in-vivo movements on the sensor. Accordingly, the amplitude fraction contributing to the fluctuation of the sensor signal in this exemplary embodiment, which is clearly related to movement effects, is reduced by the spacer from 5 to 25% of the mean signal height to 0.5 to 5% of the mean signal height.

Figure 7:
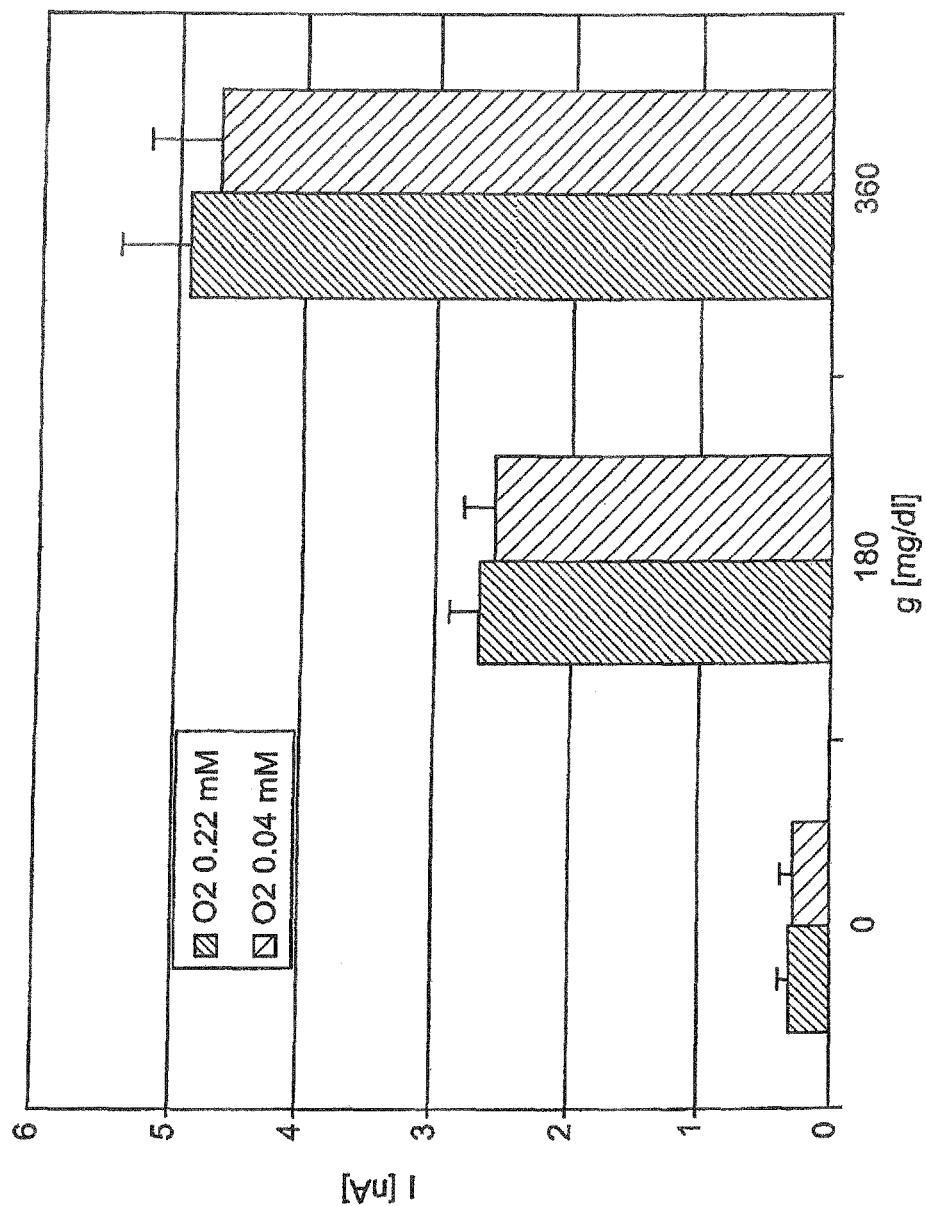
FIG. 7 shows comparative in-vitro measurements of an electrode system at various oxygen concentrations.

FIG. 7 shows a bar diagram of the current I measured under in-vitro conditions for three different glucose concentrations g, namely 0 mg/dl, 180 mg/dl, and 360 mg/dl, at two different oxygen concentrations each, namely 0.22 mmol/l (left bar in each case) and 0.04 mmol/l (right bar of the pairs of bars shown in each case). The measurements were performed for the electrode system described above, whereby the enzyme layer 5 is constructed such that a direct electron transfer is ensured. GlucDH (EC 1.1.99.17) from Acinetobacter calcoaceticus is used as the enzyme. In a first step, additional PQQ molecules are initially bound covalently to GlucDH as catalytic redox mediator, for example by adding the enzyme to PQQ acid chloride. In a second step, carbon nanotubes (NanoLab, Newton, Mass., USA; multiwall CNT, research grade) are added to a graphite-containing paste in order to improve the conductivity and porosity, this is then mixed with the PQQ-modified GlucDH, and the working electrode paste thus generated is printed onto the conductor path 1a in a distributed arrangement and then cured at 40° C. in a vacuum for 4 h. Earlier, the electrode system was provided with insulation layer 7, a reference electrode 3, and a counter-electrode 2 having a conductive layer 6. Non-immobilized enzyme is removed by rinsing with phosphate buffer. The graphite-containing paste contains a polymer binding agent, for example on the basis of polyvinyl chloride.

A cover layer 8 made of hydrophilic polyurethane (HPU, ratio of polyethylene glycol:polypropylene glycol=1:3) is dispensed three times onto the enzyme layer 5 thus produced in the form of a 2.5% ethanolic solution, and dried at room temperature for 24 h. The thickness of the cover layer thus produced is 2 µm. In order to measure the in-vitro function, the electrode systems are operated in glucose measuring solution at various oxygen concentrations at a polarization voltage of 200 mV relative to the Ag/AgCl reference electrode. The mean and standard deviation of the measuring current are calculated for each of 4 sensors. FIG. 7 shows these values for a normal oxygen saturation of the measuring solution of approximately 0.22 mmol/l and a markedly reduced oxygen concentration of 0.04 mmol/l. No relevant or significant influence of the oxygen concentration on the in-vitro function of the electrode system with direct electron transfer is observed.

Although embodiments of the invention have been described using specific terms, such description is for illustrative purposes only, and it is to be understood that changes and variations obvious to the skilled artisan are to be considered within the scope of the claims that follow and their equivalents.

LIST OF REFERENCE NUMBERS

1 Working electrode
1a Electrical conductor of working electrode
2 Counter-electrode
2a Electrical conductor of counter-electrode
3 Reference electrode
3a Electrical conductor of reference electrode
3b Silver/silver chloride layer
4 Substrate
5 Enzyme layer
6 Conductive layer
7 Insulation layer
8 Cover layer
9 Spacer
10 Potentiostat
11 Amplifier

What is claimed is:

1. Electrode system for measuring a concentration of an analyte under in-vivo conditions, the system comprising:
   a substrate;
   a counter-electrode having an electrical conductor arranged on the substrate;
   a working electrode having an electrical conductor arranged on the substrate on which an enzyme layer containing immobilized enzyme molecules for catalytic conversion of the analyte is arranged, wherein the enzyme layer is in the form of multiple fields arranged in a row or in a series at a pre-determined distance from one another on the electrical conductor of the working electrode so that the multiple fields are separate from each other; and
   a diffusion barrier that slows diffusion of the analyte from body fluid surrounding the electrode system to the enzyme molecules.

2. Electrode system according to claim 1, wherein between the fields of the enzyme layer, the electrical conductor of the working electrode is covered by an insulation layer.

3. Electrode system according to claim 1, wherein at least two of the fields of the enzyme layer are at least 5 mm distant from each other.

4. Electrode system according to claim 1, wherein a distance of at least 0.3 mm exists between neighboring fields of the enzyme layer.

5. Electrode system according to claim 1, wherein the fields of the enzyme layer each extend less than 2 mm in two directions that are perpendicular to each other.

6. Electrode system according to claim 1, wherein the diffusion barrier is in the form of a layer covering the enzyme layer.

7. Electrode system according to claim 6, wherein the diffusion barrier is made of a mixture of at least two different acrylates.

8. Electrode system according to claim 7, wherein at least one of the acrylates is a copolymer.

9. Electrode system according to claim 1, wherein the enzyme interacts with a catalytic redox mediator that is contained in the enzyme layer and reduces or prevents an oxygen dependence of the catalytic conversion of the analyte.

10. Electrode system according to claim 9, wherein the catalytic redox mediator converts hydrogen peroxide.

11. Electrode system according to claim 9, wherein the catalytic redox mediator effects a direct electron transfer.

12. Electrode system according to claim 1, wherein the enzyme layer is covered by a spacer.

13. Electrode system according to claim 12, wherein the spacer covers the working electrode and the counter-electrode in the form of a continuous layer.

14. Electrode system according to claim 1, wherein the electrical conductor of the working electrode narrows between the enzyme layer fields and the electrical conductor of the counter-electrode has a contour that follows the course of the electrical conductor of the working electrode.

15. Sensor comprising:
   an electrode system comprising:
      a counter-electrode having an electrical conductor;
      a working electrode having an electrical conductor on which an enzyme layer containing immobilized enzyme molecules for catalytic conversion of the analyte is arranged, wherein the enzyme layer is in the form of multiple fields that are arranged in a row or in a series at a pre-determined distance from each other on the electrical conductor of the working electrode so that the multiple fields are separate from each other, and wherein at least two non-neighboring fields of the enzyme layer are at least 3 mm distant from each other; and
      a diffusion barrier that slows diffusion of the analyte from body fluid surrounding the electrode system to the enzyme molecules;

a potentiostat connected to the electrode system; and an amplifier for amplification of measuring signals of the electrode system.

16. Sensor according to claim 15, wherein the electrodes of the electrode system are arranged on a substrate that carries the potentiostat or are attached on a circuit board that carries the potentiostat.

17. Sensor according to claim 15, wherein the electrical conductor of the working electrode narrows between the enzyme layer fields and the electrical conductor of the counter-electrode has a contour that follows the course of the electrical conductor of the working electrode.

18. Electrode system according to claim 1, wherein at least two of the fields of the enzyme layer are at least 3 mm distant from each other.

19. Electrode system according to claim 1, wherein the enzyme layer is applied non-continuously on the working electrode surface so that the multiple fields of the enzyme layer are separated from one another with an electrical insulating layer on the electrical conductor of the working electrode.

20. Sensor according to claim 15, wherein the enzyme layer is applied non-continuously on the working electrode surface so that the multiple fields of the enzyme layer are separated from one another with an electrical insulating layer on the electrical conductor of the working electrode.

21. Electrode system according to claim 1, wherein the working electrode has at least 5 fields of the enzyme layer.

22. Sensor according to claim 15, wherein the pre-determined distance between neighboring fields of the enzyme layer is at least 0.3 mm.

23. Sensor according to claim 15, wherein the working electrode has at least 5 fields of the enzyme layer.

24. Electrode system for measuring a concentration of an analyte under in-vivo conditions, the system comprising:

a substrate;

a counter-electrode having an electrical conductor arranged on the substrate;

a working electrode having an electrical conductor arranged on the substrate;

an enzyme layer containing immobilized enzyme molecules for catalytic conversion of the analyte, wherein the enzyme layer is in the form of multiple fields that are arranged in a row or in a series at a pre-determined distance from each other on the electrical conductor of the working electrode so that the multiple fields are separate from each other, and wherein the enzyme interacts with a catalytic redox mediator that is contained in the enzyme layer and reduces or prevents an oxygen dependence of the catalytic conversion of the analyte, and a diffusion barrier that slows diffusion of the analyte from body fluid surrounding the electrode system to the enzyme molecules.

25. Electrode system according to claim 24, wherein at least two non-neighboring fields of the enzyme layer are at least 3 mm distant from each other.

26. Electrode system according to claim 24, wherein the pre-determined distance between neighboring fields of the enzyme layer is at least 0.3 mm.

27. Electrode system according to claim 24, wherein the working electrode has at least 5 fields of the enzyme layer.

* * * * *